United States Patent [19]

Mihara et al.

[11] 4,331,444
[45] May 25, 1982

[54] COMPETITIVE IMMUNOASSAY USING SILVER HALIDE FOGGING AGENT

[75] Inventors: Yuji Mihara; Nobuhito Masuda, both of Minami-ashigara; Nobuo Hiratsuka; Takushi Miyazako, both of Tokyo; Shigeo Hirano, Minami-ashigara, all of Japan

[73] Assignee: Fuji Photo Film Co., Ltd., Kanagawa, Japan

[21] Appl. No.: 126,919

[22] Filed: Mar. 3, 1980

[30] Foreign Application Priority Data

Mar. 1, 1979 [JP] Japan ................................. 54-23963

[51] Int. Cl.³ .................. G01N 33/54; G01N 33/58
[52] U.S. Cl. .................................. 23/230 B; 23/915; 424/12
[58] Field of Search ................ 23/230 B, 915; 424/12

[56] References Cited

U.S. PATENT DOCUMENTS 3,791,932  2/1974  Schuurs ...................... 23/230 B X
4,205,952  6/1980  Cais ................................. 23/230 B Primary Examiner—Sidney Marantz
Attorney, Agent, or Firm—Sughrue, Mion, Zinn, Macpeak and Seas

[57] ABSTRACT

In a method for the immunological analysis of trace components by marking or labelling an antigen or antibody with a marker, an immune reaction is caused using an antigen or antibody marked with a fogging agent for silver halide, the labelled antigen or antibody is separated from the labelled antigen-antibody reaction product, the silver halide is developed in the presence of either one of the labelled antigen or antibody and the labelled antigen-antibody reaction product, and the density obtained is measured.

The method is comparable to radioimmunoassay in having high reproducibility and sufficient sensitivity but does not involve any risk due to radiation.

9 Claims, 1 Drawing Figure

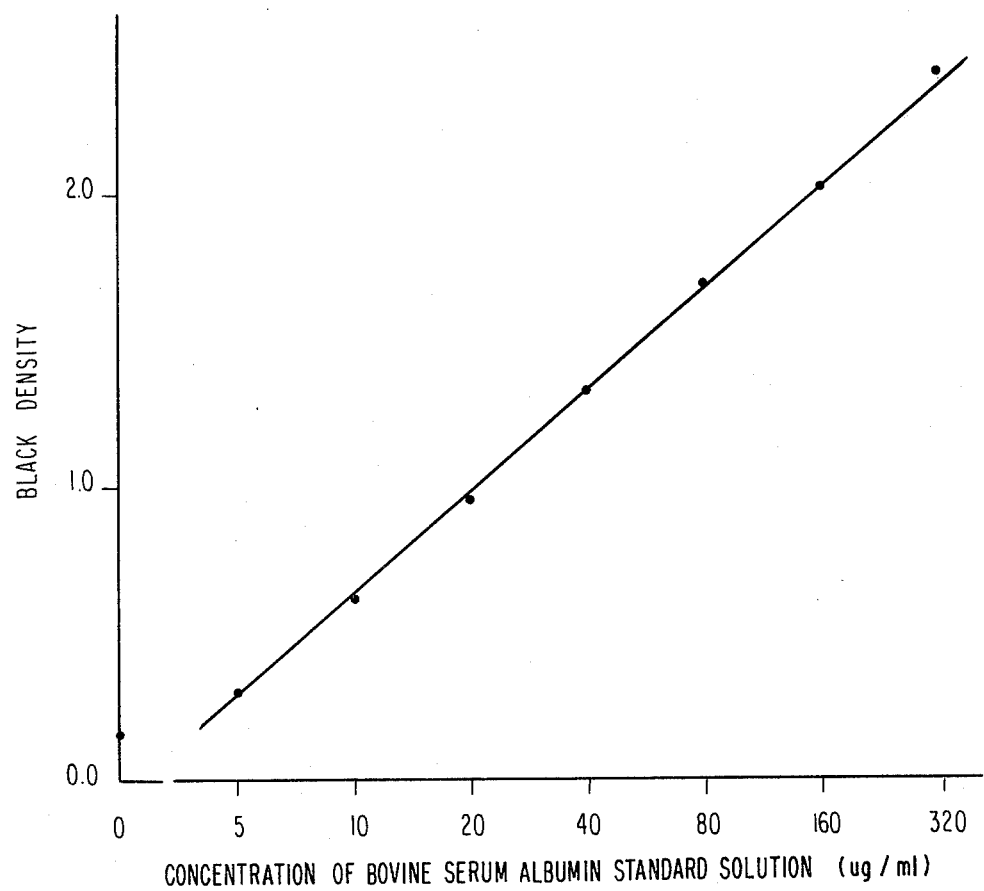

COMPETITIVE IMMUNOASSAY USING SILVER HALIDE FOGGING AGENT

BACKGROUND OF THE INVENTION

1. Field of the Invention

This invention relates to a method for immunologically analyzing trace components, more particularly, to a method for photochemically analyzing in a quantitative manner trace components utilizing immune reaction.

2. Description of the Prior Art

Radioimmunoassay (hereafter merely "RIA") is a method for the assey of trace components utilizing a specific antigen-antibody reaction. The basic principles of RIA are as follows. The reaction of a substance labelled or marked (hereafter these terms are used interchangeably) with a radioactive isotope (RI) in a given amount and a substance having a specific binding affinity thereto in a given amount results in a coupled product of both of these components, while a part of the labelled substance remains in an unbound or unreacted free state. The reaction proceeds based on the laws of mass action in general and therefore, when an unlabelled substance is added to the reaction system, binding with a limited amount of binding protein is decreased and a certain relationship (calibration curve) is established therebetween. As a result, an amount of an unknown substance can be determined from the calibration curve if the bound substance and the labelled substance in the free state are separated and either one or both are measured with respect to RI amount.

Due to the high sensitivity and the simplicity of RIA, RIA is particularly applicable to the measurement and inspection of trace amounts of proteins in blood and hormones. Details thereon are given in, e.g., Kumahara and Shizume, *New Radioimmunoassay*, pages 3 to 10, 1977, published by Asakura Publishing Co., Ltd., KISO SEIKAGAKU JIKKENHO (Basic Biochemical Experiment) (6) and SEIKAGAKUTEKI SOKUTEI (Biochemical Assay), 1967, published by Maruzen Co., Ltd., Tokyo.

However, RIA is subject to several disadvantages due to the use of RI markers ($^{125}$I, $^{131}$I, etc.) as good markers are markers having high specific radioactivity which maintain immune activity and are radioactively of high purity. For these reasons, RIA involves the danger of radiation exposure and requires the management of expensive and unstable markers which cannot be used for long periods of time. In addition, special installations, equipment and personnel qualified to deal with radiation are required. Finally, after RIA, pollution problems are encountered due to the necessity to dispose of radioactive waste.

SUMMARY OF THE INVENTION

Therefore, an object of this invention is to provide a method for determining the amount of a trace component(s) without any radiation exposure which is of sufficient sensitivity for practical use.

As a result of investigating the immunological detection and/or measurement of trace components in solution, the inventors have found that the aforesaid object can effectively be achieved utilizing a photochemical process.

Thus, the method in accordance with this invention relates to the immunological analysis of trace components present in a solution, which comprises marking or labelling an antigen or antibody with a silver halide fogging agent, i.e., a compound which has the capability to fog silver halide, developing silver halide in the presence of the fogging agent bound to the antigen or antibody, and then determining the resulting density of the amount of silver or the amount of dye formed.

BRIEF DESCRIPTION OF THE DRAWING

The FIGURE shows a calibration curve for use of quantitative analysis of albumin, obtained in Example 1.

DESCRIPTION OF THE PREFERRED EMBODIMENTS

More specifically, a known amount of a labelled antigen or labelled antibody is reacted with an antigen and/or antibody. After separating the reaction product from the reaction system, a quantitative measurement of the marker is performed using silver halide to generate a calibration curve. Based on the calibration curve, an unknown amount of the antigen or antibody can then be measured.

In the measurement method of the present invention, no light "exposure" prior to development is necessary, as will be apparent from the above disclosure.

In this invention, the fogging agent or agents used to mark an antigen or antibody, i.e., the substance(s) capable of fogging silver halide, are known as chemical sensitizers for photography and typically include sulfur-containing compounds, reducible compounds, metal complexes, etc.

Details on useful fogging agents are given in. e.g., *The Theory of the Photographic Process*, fourth ed., edited by T. H. James, pages 393 to 395, 1977, published by Macmillan Publishing Co. More specifically, fogging agents can be classified into the following groups:

1. Compounds having a cyclic or non-cyclic thiocarbonyl group (e.g., thiourea, dithiocarbamates, trithiocarbonates, dithio esters, thioamides, rhodanines, thiohydantoins, thiosemicarbazides and derivatives thereof).
2. Compounds having a cyclic and non-cyclic thio ether group (e.g., sulfides, disulfides, polysulfides, etc.).
3. Other sulfur-containing compounds (e.g., thiosulfuric acid, thiophosphoric acid and compounds derived therefrom).
4. Nitrogen-containing reducible compounds (e.g., hydrazine, hydrazone, amines, polyamines, cyclic amines, hydroxylamine, quaternary amine salt derivatives, etc.).
5. Reducible compounds (e.g., aldehydes, sulfonic acids, enediols, metallic hydride compounds, alkylated metals, aromatic dihydro compounds, active methylene compounds, etc.).
6. Metal complexes (e.g., a tetra-coordination Ni(II) complex having sulfur as a ligand, an Fe(II) complex, etc.), and
7. Acetylene compounds
8. Others (phosphonium salts, etc.)

Of these compounds, groups 4, 5, and 6, are most preferred and groups 1, 2, 7 and 3 are second most preferred, in this order.

More specifically, the following compounds are particularly preferably employed in this invention:

4-a. Hydrazines

R—NH—NH—R'

R, R': aliphatic, aromatic and heterocyclic residues, acyl, sulfonyl, alkoxycarbonyl or substituents thereof (R and R' may be the same or different).

e.g., 4-(2-formylhydrazino)phenylisothiocyanate; specific examples of these hydrazines are described in Japanese Patent Application Laid Open (OPI) No. 53-81120, West German Pat. No. 1,597,493, Japanese Patent Publication No. 46-22515, U.S. Pat. Nos. 2,663,732, 2,618,656, 2,563,785, 2,588,982, 2,604,400, 2,675,318, 2,685,514, and 3,227,552, British Pat. No. 1,269,640, French Pat. No. 2,148,902, U.S. Pat. Nos. 4,080,207, 4,030,925 and 4,031,127, Research Disclosure No. 17626 published December in 1978, No. 176, West German Patent Application (OLS) No. 2,719,371, Japanese Patent Application Nos. 52-142469, 53-125602 and 53-148522, Japanese Patent Application Laid Open (OPI) No. 53-125,062, etc.

4-b. Hydrazones

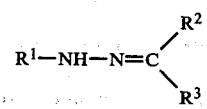

$R^1$, $R^2$, $R^3$: aliphatic, aromatic and heterocyclic residues, acyl, sulfonyl, alkoxycarbonyl or substituents thereof; e.g., 2-(2-isopropylidenehydrazino)phenyl isothiocyanate; specific examples of other hydrazones are given in U.S. Pat. Nos. 3,227,552 and 3,615,615, Japanese Patent Application Laid Open (OPI) No. 52-3426, Japanese Patent Publication 51-1416, etc.

5-a. Aldehydes

R has the same meaning as defined above. Specific examples of useful aldehydes are provided in Japanese Patent Application Laid Open (OPI) No. 47-9678, Japanese Patent Publication Nos. 52-19452 and 49-20088, etc. A particularly preferred compound is:

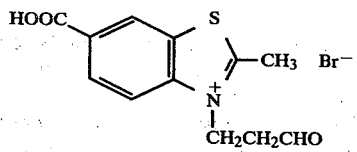

5-b. Metallic hydride compounds

There can be used in this invention compounds as disclosed in Japanese Patent Publication No. 45-28065, U.S. Patent Applications (DAS) 3,951,665 and 3,804,632, British Pat. No. 821,251, etc., 5-c. Dihydro compounds In this invention, compounds as described in U.S. Pat. No. 3,951,656, Belgian Patent 708,563, West German Patent Nos. 1,572,125 and 2,104,161, British Pat. No. 1,282,084, British Pat. No. 1,308,753, West German Patent Application (OLS) No. 1,572,140, etc. can advantageously be employed.

8. Acetylene compounds

R has the same meaning as defined above. A particularly useful compound is:

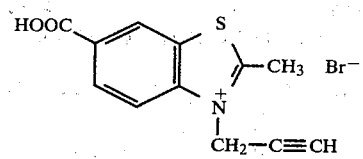

In addition, compounds as described in West German Patent Application (OLS) No. 2,655,870 can effectively be employed in this invention.

These fogging agents can be used singly or in combination. The fogging agents can also be employed in the form of a precursor which will form these fogging agents through chemical reaction during development processing.

In the present invention, any method of chemically binding a fogging agent to an antigen or antibody can be utilized, e.g., a chemical reaction such as an addition reaction, a substitution reaction, a Schiff's base forming reaction, etc., are effective for labelling.

As particularly preferred methods, marking methods as are conventionally employed for enzyme immunoassay and fluorescent immunoassay (see Fukashi Miyai, RINSHOKENSA (Clinical Test), 22, 1219 (1978)) and conventional methods for hardening a photographic emulsion gelatin layer can be used.

Types of bonds between the antigen or antibody and fogging agent formed include:

(1) a bond formed by direct reaction between the fogging agent having a functional group(s) and the antigen or antibody having a functional group(s), (2) a bond formed through a compound having two or more of the above functional groups, and (3) a bond formed between the fogging agent and the antigen or antibody after activating these functional groups using an activating agent as later disclosed.

In these methods, the following conditions should be met:

(A) Anitgen-antibody activity should be maintained even after labelling;

(B) At least either one of the bound labelled substance and labelled free substance (antigen-antibody complex) be maintained with an action of fogging silver halide emulsion, and the like.

That is, the reaction temperature is generally between $-20°$ and $60°$ C., preferably $-8°$ and $40°$ C., the reaction time is generally between 10 mins. and 16 hours; and the reaction pressure is between 1 and 20 atms., preferably atmospheric pressure. Where materials that tend to be volatile are employed, it will be necessary that the reaction pressure be raised to, e.g., 20 atms. It is preferred that water or a pH buffering solution be employed as a solvent. Organic solvents such as DMF, methylene chloride, etc., are optionally used. These reaction conditions are generally common to those available for chemical decoration modification of proteins and enzymes and are described in, e.g., PROTEIN, NUCLEIC ACID & ENZYME, 10, 1127(1970), entitled "Chemical Modification of Enzyme and Protein—List of Publications for Respective Amino Acid Residues" by Soji Rokushika et al, and SEIKAGAKU JIKKEN KOZA (Lecture on Biochemical Experiments) I, 4th separate volume, pp. 10–203 (1977) edited by Nihon Kagakukai, published by Tokyo Kagaku Dojin, entitled "Chemical Modification of Protein".

Antigen or antibody materials containing reactive groups which provide bond formation as above described and the reactions thereof are described in detail in SHINSEIKAGAKU KOZA (Lecture on New Biochemistry), 1, entitled "Chemistry of Protein", edited by Nihon Seikagakukai, published by Tokyo Kagaku Dojin, 1977; Izumiya PEPTIDE GOSEI (Synthesis of Peptide), etc. One skilled in the art can easily perform such reactions for forming bonds from knowledge in the art and these publications.

Typical examples of activating agents used in (2) above include alkyl chloroformates (e.g., diethyl chloroformate, isobutyl chloroformate, etc.) and sulfonic acid esters (e.g., alkane sulfonic acid esters, etc.).

Exemplary functional groups of the antigen or antibody which react with the fogging agent(s) include an amino group, an imino group, a hydroxy group, a mercapto group, a carboxy group, a carboxylic acid amido group, etc. These functional groups can inherently be present in the antigen or antibody or, alternatively, these groups or compounds containing these groups can be introduced into the antigen or antibody through chemical reaction. Further, these functional groups can be employed singly or in combination.

Groups present in the fogging agent that react with the aforesaid functional groups include:

alkyl chloroformates (e.g., diethyl chloroformate, isobutyl chloroformate, etc.) aldehydes (e.g., formaldehyde, glutaraldehyde, etc.), isocyanates (e.g., xylylene diisocyanate, tolylene diisocyanate, hexamethylene diisocyanate, etc.), thioisocyanates (e.g., xylylene dithioisocyanate, etc.) vinyl compounds (e.g., divinyl ketone, methylene bisacrylamide, divinylsulfone, etc.), active halides (e.g., cyanuric chloride, mucohalogenic acids, nitrophenyl chloride, phenol-2,4-toluenesulfonate, etc.), imidazoleamides (e.g., carbonyl diimidazole, sulfonyl diimidazole, triimidazolyl phosphate, etc.), pyridinium compounds (e.g., N-carbamoyl pyridinium, N-carbamoyloxypyridinium, etc.), sulfonic acid esters (e.g., alkane sulfonic acid esters, etc.), bismaleimides (e.g., N,N'-(1,3-phenylene)-bismaleimide, etc.), diazonium compounds (e.g., bisdiazobenzidine, etc.), epoxy compounds (e.g., bisoxysilane, etc.), acid anhydrides, carboxylic acids, ethyleneimines, and the like.

These functional groups can inherently be present in the fogging agents or can be introduced into the fogging agents via chemical reaction(s) directly or using compounds having these functional groups.

Furthermore, the fogging agent can be cross-linked and combined with an antigen or antibody using a compound (reagent) having two or more functional groups (preferably 2 to 5).

All of the above functional groups can be used singly or in combination.

Further, the above functional groups for the antigen, antibody or marker can also be activated with carbodiimides (e.g., 1-ethyl-3-(3-dimethylaminopropyl)carbodiimide, 1-cyclohexyl-3-(2-morphodinyl-4-ethyl)carbodiimide, N,N'-dicyclohexylcarbodiimide, etc.), isoxazoliums, psuedo bases, active esters (e.g., benzenesulfonic acid hydrosuccinimide ester, etc.), followed by marking the antigen or antibody therewith.

In this invention, the amount of the fogging agent(s) used for marking or labelling varies depending upon the antigen(s) or antibody(s) employed and is not critically limited; generally, however, the fogging agent(s) is (are) 1 to 700 hundred times that of the antigen or antibody, preferably 1 to 100 times, same basis.

Simple tests will be enough to confirm completion of labelling with the fogging agent. One typical method is that, where labelling is completed, silver halide is fogged and such can be seen by the naked eye after processing. Another method for confirming the labelling being effected is to analyze the presence or absence of the specific terminal groups, e.g., an amino or carboxy group(s). In the case that the fogging agent is introduced at the terminal amino group(s) of antigen or antibody, the labelling reaction can be confirmed by analysis of the N-terminal. The completion of the labelling reaction has been effected if the amino acid(s) corresponding to an amino group(s) on which labelling is to occur are not detectable. Detailed disclosure on such an N-terminal analysis is described in, e.g., B. S. Hartley et al., *Biochim. Biophys. Acta*, 21, 58 (1956) (generally referred to as a Dansyl method in the art), *Archn. Biochem. Biophys.*, 22, 475 ((1949) (a PTC (phenol isocyanate) method), F. Sanger, *Biochem. J.*, 39, 507(1945) (a dinitrofluorobenzene method), etc. In a similar manner, the terminal carboxy group(s) are analyzed to check completion of the labelling reaction, details of which are given in, e.g., S. Akabori, K. Ohno and K. Narita, *Bull. Chem. Soc. Japan*, 25, 214 (1952) (generally referred to as a hydrazine decomposition method in the art), H. Matuo, U. Fujimoto and T. Tatuno, *Biochem. Biophs. Res. Communication*, 22, 69 (1966) (a tritium marking method), etc. Further, details of these terminal determination methods are also given as a review in S. B. Needleman, *PROTEIN SEQUENCE DETERMINATION*, published by Springer Verlag (Berlin), 1975.

The details of these reactive groups and reactions utilizing these groups are described in *SHINSEIKAGAKU JIKKEN KOZA* (Lectures on New Biochemical Experiment), 1. Chemistry of Protein, edited by Nippon Seikagakuka, 1977, published by Tokyo Kagaku Dojin Publishing Co., Ltd., *PEPTIDE GOSEI* (Synthesis of Peptide), Izumiya, published by Maruzen Co., Ltd., etc.

To separate the marked or labelled antigen-antibody reaction product or antigen-bound antibody (B) from the labelled free antigen or antibody (F) (hereafter this separation is often referred to as B/F separation) in this invention, various liquid chromatography techniques (gel filtration, ion exchange, partition chromatography, adsorption chromatography (including affinity chromatography), microfilter filtration, dialysis, adsorption using cellulose, talc, dextran powder, etc., salting out, precipitation, centrifugation, crystallization, extraction, solid phase separation, etc.) can be used.

Specific examples of methods for bringing the fogging agent combined with the antigen or antibody or with the antigen-bound antibody into contact with the silver halide(s) include dropping the aforesaid substances onto the surface of an emulsion containing silver halide(s), dropping the aforesaid substances onto an emulsion solution containing silver halide(s), or other methods of contacting the aforesaid substances with the surface of an emulsion containing silver halide(s), etc. Of these methods, dropping the aforesaid substances into the surface of an emulsion containing silver halide(s) is preferred. The silver halide(s) fogged by these methods or emulsions containing such silver halide(s) can be, depending upon necessity, coated onto a support such as paper, cellulose acetate, polyester, etc.

Trace components which can be detected and/or measured by the method of this invention typically include trace components in the living body, but drugs, in addition thereto, can also be detected and/or measured.

Specific examples of such trace components include peptide hormones (e.g., insulin, glucagon, parathyroid hormone, carcitonin, erythropoetin, secretin, cholecystokinin, gastrin, angiotensin II, vasopressin, oxytocin, melanin cell-stimulating hormone, adrenal cortex stimulating hormone, thyroid stimulating hormone, growth hormone, prolactin, corpus luteum stimulating hormone, follicle stimulating hormone); non-peptide hormones (e.g., steroid hormones such as glucocorticoid, aldosterone, adrenergic androgene, estrogen, progesterone, testosterone); other hormones such as thyroid hormones (e.g., thyroxin, triiodothyronine), cortisol, estriol, adrenalin, noradrenalin, melatonin, acetylcholine; enzymes such as $C_1$-esterase, alkali phosphatase, pepsinogen, tripsin; kinase virus; specific antigens; tumor antigens (e.g., α-fetoprotein); blood serum protein components (e.g., thyroxin-bound globulin, IgG, IgE); drugs (e.g., LDS, etc.) and others (e.g., rheumatism factor, myocin, etc.).

Specific examples of silver halides employed in ths invention include silver chloride, silver chlorobromide, silver bromide, silver iodobromide, silver chloroiodobromide, silver chloroiodide, silver iodide, etc.

These silver halides can be emulsion dispersed or suspended in a hydrophilic colloid binder solution or can be supported on a support without any binder (e.g., a silver halide layer can be directly formed on a support by vacuum deposition, etc.).

Silver halide(s) contained in a photographic emulsion used in the present invention can be prepared in a conventional manner, e.g., by a single jet method, a double jet method, or a combination thereof. Useful preparation methods of silver halide emulsions are described in, e.g., Trivelli and Smith, *The Photographic Journal*, vol. 79, pp. 330–338 (1939), C. E. K. Mees, *The Theory of the Photographic Process*, published by MacMillan, Glafkides, *Photographic Chemistry*, Vol. I, pp. 327–336, published by Fountain Press, etc.

The grain size of the silver halide(s) in an emulsion employed in this invention is conventional or smaller; it is thus generally preferred that the average grain diameter be 0.04 to 4 microns (measurement by the projected area method).

The silver halide emulsions employed in this invention are not chemically ripened but generally are chemically sensitized in a conventional manner, for example, by gold sensitization (as disclosed in U.S. Pat. Nos. 2,540,085, 2,597,876, 2,597,915 and 2,399,083, etc.), by sensitization with one or more metal ions from Group VIII of the Periodic Table, by sulfur sensitization (as disclosed in U.S. Pat. Nos. 1,574,944, 2,278,947, 2,440,206, 2,410,689, 3,189,458 and 3,415,649, etc.), by reduction sensitization (as disclosed in U.S. Pat. Nos. 2,518,698, 2,419,974 and 2,983,610, etc.) or by a combination thereof.

Specific examples of chemical sensitizers include sulfur sensitizers such as allylthio carbamide, thiourea, sodium thiosulfate cystine, etc.; noble metal sensitizers such as potassium chloroaurate aurous thiosulfate, potassium chloropalladate, etc.; reduction sensitizers such as stannous chloride, phenylhydrazine, reductone, etc.; polyoxyethylene derivatives as described in British Pat. No. 981,470, Japanese Patent Publication No. 31-6475 and U.S. Pat. No. 2,716,062, etc.; polyoxypropylene derivatives, quaternary ammonium-containing derivatives, etc.

Silver halide emulsions employed in this invention can contain conventional antifoggants and stabilizers. From the view of improving contrast of the labelled and thus fogged area to the unlabelled and thus non-fogged area, the use of antifoggants is desired. That is, the fogging agent bound to an antigen or antibody is dropped onto a limited area of the photographic element and thus causes fog at the limited area; accordingly, it is desired that the background or non-fogged areas be not fogged, and such is effected by incorporating antifoggants into silver halide emulsions, in general. For example, specific antifoggants and stabilizers include thiazolium salts as described in U.S. Pat. Nos. 2,131,038 and 2,693,716, etc.; azaindenes as described in U.S. Pat. Nos. 2,886,437 and 2,444,605, etc.; urazoles as described in U.S. Pat. No. 3,287,135, etc.; sulfocatechols as described in U.S. Pat. No. 3,236,652, etc.; oximes as described in U.S. Pat. Nos. 2,403,927, 3,266,897 and 3,397,987, etc.; nitron; nitroindazoles; polyvalent metal salts as described in U.S. Pat. No. 3,220,839, etc.; and salts of palladium, platinum and gold as described in U.S. Pat. Nos. 2,566,263 and 2,597,915, etc.

Silver halide emulsions used in this invention can also contain, if desired, one or more developing agents (e.g., hydroquinones, catechols, aminophenols, 3-pyrazolidones, ascorbic acid or derivatives thereof, reductones, phenylenediamines, etc.), or combination of these developing agents. The developing agents can be incorporated into a light sensitive emulsion and/or other suitable layers of a photographic element. The developing agents can be incorporated therein using a suitable solvent or in the form of a dispersion as described in U.S. Pat. No. 2,592,368 or French Pat. No. 1,515,778.

Silver halide emulsions employed in this invention can also contain, if desired, coating aids such as saponin, alkyl aryl sulfonates as described in U.S. Pat. No. 2,600,831, etc.; amphoteric compounds as described in U.S. Pat. No. 3,133,816, etc. and can further contain antistatic agents, plasticizers, fluorescent whitening agents, developing accelerating agents, air antifogging agents, color toning agents, etc.

As the silver halide emulsion(s) used in this invention, gelatino silver halide emulsions are generally employed but this is not mandatory. For example, instead of gelatin, substances that do not adversely affect light sensitive silver halides such as albumin, agar, gum arabic, alginic acid, acylated gelatin (e.g., phthalated gelatin, malonated gelatin, etc.), hydrophilic polymers such as polyvinyl alcohol, polyvinylpyrrolidone, polyacrylamide, polystyrene sulfonic acid, cellulose compounds (e.g., hydroxyethyl cellulose, carboxymethyl cellulose, dextrin etc.), water-soluble starch, etc., can be used. Further, combinations thereof can be used.

Photographic emulsion layers of photographic light sensitive materials which can be used in this invention can contain color image-forming couplers, that is, compounds capable of forming dyes by reaction with the oxidation product of an aromatic amine (normally a primary amine) developing agent (hereafter referred to as a coupler). It is preferred that the coupler be non-diffusible and comprise a hydrophobic group(s) called a ballast group(s) in the molecule thereof. The couplers can be either four-equivalent or two-equivalent to silver ions. In addition, the photographic emulsion layers can also contain colored couplers having a color correction effect or couplers releasing a development inhibitor upon development (DIR couplers). The couplers can also be couplers where the product of coupling reaction is colorless.

As yellow color-forming couplers, known open chain ketomethylene type couplers can be used. Of these, benzoylacetanilide type and pivaloyl acetanilide type compounds are preferred. Specific examples of yellow-color-forming couplers are described in U.S. Pat. Nos. 2,875,057, 3,265,506, 3,408,194, 3,551,155, 3,582,322, 2,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 51-10783 Japanese Patent Application Laid Open (OPI) Nos. 47-26133, 48-73147, 51-1026366, 50-6341, 50-123342, 60-130442, 50-21827, 50-87650, 52-82424 and 52-115219, etc.

As magenta color-forming couplers, pyrazolone type compounds, indazolone type compounds, cyanoacetyl compounds, etc., are preferred and of this, pyrazolone type compounds are particularly preferred. Specific examples of magenta color-forming couplers which can be employed are those described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication Nos. 40-6031 and 51-45990, Japanese Patent Application Laid Open (OPI) Nos. 51-20826, 52-58922, 49-129538, 49-74027, 50-159336, 52-42121, 49-74028, 50-60233, 51-26541 and 53-55122, etc.

As cyan color-forming couplers, phenol type compounds, naphthol type compounds, etc., are preferred. Specific examples include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application Laid Open (OPI) Nos. 48-59838, 51-26034, 48-5055, 51-146828, 52-69624 and 52-90932, etc.

As colored couplers, those described in, e.g., U.S. Pat. Nos. 3,476,560, 2,521,908 and 3,034,892, Japanese Patent Publication Nos. 44-2016, 38-22355, 42-11304 and 44-32461, Japanese Patent Application Laid Open (OPI) No. 2,418,959, etc., can be used.

As DIR couplers, those described in e.g., U.S. Pat. Nos. 3,227,554, 3,617,291, 3,701,783, 3,790,384 and 3,632,345, West German Patent Application (OLS) Nos. 2,414,006, 2,454,301 and 2,454,329, British Pat. No. 953,454, Japanese Patent Application Laid Open (OPI) Nos. 52-69624, 49-122335 and 52-69624 and Japanese Patent Publication No. 51-16141 can be employed.

Compounds releasing development inhibitors with development can also be present in addition to DIR couplers. For example, the compounds described in U.S. Pat. Nos. 3,297,445 and 3,379,529, West German Patent Application (OLS) No. 2,417,914 and Japanese Patent Application Laid Open (OPI) Nos. 52-15271 and 53-9116 can be employed.

The aforesaid couplers can be incorporated in the same layer or in two or more different layers. The same compound can also be present in two or more different layers.

These couplers are generally added to an emulsion layer in an amount of $2 \times 10^{-3}$ to $5 \times 10^{-1}$ mol per 1 mol of silver, preferably $1 \times 10^{-2}$ to $5 \times 10^{-1}$ mol, same basis.

To introduce the aforesaid couplers into a silver halide emulsion layer, conventional methods as described in U.S. Pat. No. 2,322,027 can be employed. For example, these couplers can be dissolved in high boiling point solvents such as an alkyl phthalate(s) (dibutyl phthalate, dioctyl phthalate, etc.), a phosphoric acid ester(s) (diphenyl phosphate, triphenyl phosphate, tricresyl phosphate, dioctyl butyl phosphate), a citric acid ester(s) (e.g., tributyl acetylcitrate, etc.), a benzoic acid ester(s) (e.g., octyl benzoate, etc.), an alkylamide(s) (e.g., diethyl lauryl amide), a fatty acid ester(s) (e.g., dibutoxyethyl succinate, dioctyl azelate, etc.), or into an organic solvent(s) having a low boiling point of about 30° to about 150° C., e.g., a lower alkyl acetate such as ethyl acetate, butyl acetate, etc., or into ethyl propionate, secondary butyl alcohol, methyl isobutyl ketone, beta-ethoxyethyl acetate, methyl cellosolve acetate, etc.; the solution is then dispersed in the hydrophilic colloid(s). The aforesaid high boiling point organic solvent(s) can also be used in combination with the aforesaid low boiling point organic solvent(s).

Where couplers contain an acid group(s) such as a carboxylic acid or sulfonic acid group, they are introduced into the hydrophilic colloid(s) as an aqueous alkaline solution.

In addition to the above high boiling point organic solvents, other high boiling point organic solvents can also be employed, and specific examples thereof include those described in, e.g., U.S. Pat. Nos. 2,322,027 2,533,514 and 2,835,579; Japanese Patent Publication No. 46-23233; U.S. Pat. No. 3,287,134; British Pat. No. 958,441; Japanese Patent Application Laid Open (OPI) No. 47-1031; British Patent No. 1,222,753; U.S. Pat. No. 3,936,303, Japanese Patent Application Laid Open (OPI) Nos. 51-26037 and 50-82078; U.S. Pat. Nos. 2,353,262, 2,852,383, 3,554,755, 3,676,137, 3,676,142, 3,700,454, 3,748,141 and 3,837,863; West German Patent Application (OLS) No. 2,538,889, Japanese Patent Application Laid Open (OPI) Nos. 51-27921, 51-27922, 51-26035, 51-26036 and 50-62632, Japanese Patent Publication No. 49-29461, U.S. Pat. Nos. 3,936,303, 256,658; Japanese Patent Application Laid Open (OPI) No. 53-1521, etc.

Development processing performed in this invention is conventional. For example, where emulsions are coated onto a support, development can be carried out in accordance with methods conventionally used for photographic development. More specifically methods of development processing conventional photographic films or printing paper, etc., can be employed.

In addition, development and other photographic processing can also be carried out by extending onto, coating onto, immersing in or spraying onto a support having coated thereon an emulsion various photographic processing agents. Further, where an emulsion is in the liquid state, photographic processing can be performed by adding to and mixing with the liquid emulsion the desired photographic agents.

As processing solutions employed in development processing in this invention, known processing solutions are typically employed. The processing temperature is generally between 18° and 50° C., but can be lower than 18° C. or higher than 50° C. Depending upon the purpose, any development processing for forming silver images (black-and-white photographic processing) or color photographic processing comprising development processing to form color images can be used.

Developing solutions used in the case of black-and-white photographic processing generally contain known developing agents. As such developing agents, dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds comprising a condensed 1,2,3,4-tetrahydroquinoline ring and an indolene ring as described in U.S. Pat. No. 4,067,872, etc., can be used singly or in combination.

Development processing performed in this invention is conventional and details thereof are given in L. F. Mason, *PHOTOGRAPHIC PROCESSING CHEMISTRY*, The Focal Press (1966), T. H. James, and in *THE THEORY OF THE PHOTOGRAPHIC PROCESS*, 4th edition, pages 291-334 and pages 373-403 (1977), Macmillan Publishing Co., Inc. (1977). That is, where an emulsion(s) is coated onto a support, development can be carried out in accordance with methods conventionally used for photographic development. More specifically, methods of development processing conventional photographic films or printing paper, etc., can be employed. For example;

(1) color development→stop→bleach→wash→fix→wash→stabilization→dry, (2) color development→stop→bleach→fix→wash→stabilization→dry, (3) color development→stop-fix→bleach→fix→wash→stabilization→dry, or (4) color development→bleach→wash→fix→wash→stabilization→dry.

In processings (1) to (4), a pre-bath, a hardening bath, etc., may be employed before the color development and also a stabilization or a wash after bleach may be omitted.

(5) black and white development→stop→bleach→wash→fix→wash→stabilization→dry, (6) black and white development→stop→fix→wash→stabilization→dry, (7) black and white development→stop-fix→fix→wash→stabilization→dry, (8) black and white development→wash→fix→wash→stabilization→dry.

On the other hand, processings for color reversal films are fundamentally composed of the following steps:

(9) black and white development→stop→wash→fogging→wash→color development→stop→wash→bleach→wash→fix→wash→stabilization→dry or

(10) black and white development→stop→wash→fogging→wash→color development→stop→wash→bleach→fix→wash→stabilization→dry.

Developing solutions having the compositions as indicated in the examples hereinafter are typically used in the above processings.

Typical examples of fixing solutions and bleaching solutions are shown below.

| Composition of Fixing Solution: | | |
|---|---|---|
| | Acidic-Non-Hardening Type | Acidic-Hardening Type |
| Water (ml.) | 500 | 600 |
| Sodium thiosulfate (g) | 240 | 240 |
| Sodium thiosulfite, anhydrous (g) | 10 | 15 |
| Sodium hydrogen | | |

| -continued | | |
|---|---|---|
| Composition of Fixing Solution: | | |
| | Acidic-Non-Hardening Type | Acidic-Hardening Type |
| sulfite (g) | 25 | — |
| Acetic acid (28%) (ml.) | — | 48 |
| Boric acid (g) | — | 7.5 |
| Potassium alum (g) | — | 15 |
| Water to make | 1 liter | 1 liter |

| Composition of Bleaching Solution: | | |
|---|---|---|
| Kind | Major Ingredient | Application |
| Simple bleaching solution | acidic bichromates | black-and-white reversal |
| Rehalogenation bleaching solution | ferricyanides - potassium bromide | color reversal |
| Blix solution | $Fe^{3+}$ - EDTA - thiosulfates | color paper |
| Bleach-stabilization solution | ferricyanides - thiocyanates | stabilization, no coloration |

The developing solutions generally also contain known preservatives, alkali agents, pH buffers, antifogging agents, and, if necessary, dissolution aids, color toning agents, development accelerators, surface active agents, defoaming agents, softening agents, hardening agents, viscosity-imparting agents, etc.

"Lith" type development processing can also be applied to the photographic emulsion of this invention. The term "lith" type development processing refers to development processing which comprises, for the purpose of photographic reproduction of line images or photographic reproduction of half tone images using dots, infectious development at a low concentration of sulfite ions generally using a dihydroxybenzene(s) as a developing agent, the details of which are given in *Photographic Processing Chemistry*, Mason, 163-165 (1966).

As a special aspect of development, a developing method which comprises treating a light sensitive material in which a developing agent is contained, e.g., in an emulsion layer, in an aqueous alkaline solution can be used. Of such developing agents, a hydrophobic type can be incorporated into an emulsion layer by latex dispersion, as disclosed in *Research Disclosure*, No. 169, RD-16928. Such development processing can also be used in combination with silver salt stabilization, e.g., with a thiocyanate(s).

As fixing solutions, those having compositions conventionally used in photographic processing can be employed, e.g., as fixing agents, organic sulfur compounds such as thiosulfates, thiocyanates and other organic sulfur compounds that are known as having a fixing effect can be employed. The fixing solution can also contain water soluble aluminum salts as a hardening agent.

To form dye images, again conventional methods are used. A nega-posi method (e.g., as described in *Journal of the Society of Motion Picture and Television Engineers*, vol. 61, 667-701 (1953) can also be used; further, a color reversal method which comprises developing with a developer containing a black-and-white developing agent to form negative silver images, then performing at least one overall exposure or other suitable fogging treatment and subsequently color developing to obtain positive color images can also be used; also, a silver dye bleach method which comprises exposing a photographic emulsion layer containing a dye, developing to thereby form silver images, and then bleaching the dye using the silver images as a bleaching catalyst, etc., can be used.

In general, a color developer comprises an aqueous alkaline solution containing a color developing agent. As color developing agents, known primary aromatic amine developing agents, for example, phenylenediamines (e.g., 4-amino-N,N-diethylaniline, 3-methyl-4-amino-N,N-diethylaniline, 4-amino-N-ethyl-N-beta-hydroxyethylaniline, 3-methyl-4-amino-N-ethyl-N-beta-hydroxyethylaniline, 3-methyl-4-amino-N-ethyl-N-beta-methanesulfamidoethylaniline, 4-amino-3-methyl-N-ethyl-N-beta-methoxyethylaniline, etc.) can be used.

In addition, compounds as described in L. F. A. Mason, *Photographic Processing Chemistry*, pages 226–229, 1966, Focal Press; U.S. Pat. Nos. 2,193,015 and 2,592,364; and Japanese Patent Application Laid Open OPI No. 48-64933, etc., can be used.

The color developer can also contain a pH buffering agent such as a sulfite, carbonate, borate and phosphate of an alkali metal, a development inhibitor or an antifogging agent such as a bromide, iodide or an organic antifogging agent, etc. The color developer can also contain, if necessary, a hard water softner, a preservative such as hydroxylamine, an organic solvent such as benzyl alcohol or diethylene glycol; a development accelerator such as polyethylene glycol, a quaternary ammonium salt or an amine; a dye forming coupler, a competing coupler, a fogging agent such as sodium borohydride, an auxiliary developing agent such as 1-phenyl-3-pyrazolidone, a viscosity imparting agent, a polycarboxylic acid type chelating agent as described in U.S. Pat. No. 4,083,723, an antioxidant as described in German Patent Application (OLS) No. 2,622,950, etc. Of course, combinations of the above materials can also be used.

The photographic emulsion layer after color development are usually subjected to bleaching. Bleaching can be performed with fixing at the same time or separately therefrom. Representative examples of bleaching agents include polyvalent metal compounds of iron (III), cobalt (III), chromium (VI), copper (II), etc., peroxides, quinones, nitroso compounds, etc. For example, ferricyanides, bichromates, inorganic complexes of iron (III) or cobalt (III), aminopolycarboxylic acids such as ethylenediamine tetraacetic acid, nitrilotriacetic acid, 1,3-diamino-2-propanol tetraacetic acid, etc., complexes of organic acids such as citric acid, tartaric acid, leic acid, etc.; persulfates, permaganates; nitrosophenol, etc., can be employed. Of these, potassium ferricyanide, ethylene diamine tetraacetic acid iron (III) sodium and ethylene diamine tetraacetic acid iron (III) ammonium are particularly useful both in an independent bleaching solution and in a mono bath bleaching-fixing solution.

The bleaching or blix solutions can also contain bleach accelerators as described in U.S. Pat. Nos. 3,042,520 and 3,241,966 and in Japanese Patent Publication Nos. 45-8506 and 45-8836, etc., thiol compounds as described in Japanese Patent Application Laid Open (OPI) No. 53-65732 and other various additives.

Processing solutions which are used in this invention can be liquid compositions containing processing components necessary for the development of silver halide emulsions and the formation of diffusion transfer dye images in which the major portion of the solvent is water and wherein a hydrophilic solvent(s) such as methanol, methyl cellosolve, etc., can also optionally be present in addition to water.

The processing compositions should have a pH necessary for development of the emulsion layers and should contain alkali in an amount sufficient to neutralize acids (e.g., hydrogen halides such as hydrogen bromide, carboxylic acids such as acetic acid, etc.) released during various steps for developing and forming dye images. As the alkali, alkali metal or alkaline earth metal salts, e.g., lithium hydroxide, sodium hydroxide, potassium hydroxide, a calcium hydroxide dispersion, hydroxylated tetramethyl ammonium, sodium carbonate, trisodium phosphate, diethyl amine, etc., or other amines are illustrative. Preferably, the alkali is an alkali hydroxide and imparts a pH of at least about 12 at room temperature, more preferably a pH of at least 14.

More preferably, the processing compositions contain hydrophilic polymers such as high molecular weight polyvinyl alcohol, hydroxyethyl cellulose, sodium carboxymethyl cellulose and the like. These polymers impart a viscosity of at least 1 poise at room temperature, preferably several hundred (500 to 600) to 1000 poise to the processing compositions to thereby not only provide uniform development upon processing but also to permit easy transfer of aqueous solvent into the light sensitive element and an image receiving element during processing, whereby, when the processing compositions are condensed, a non-fluid layer can be formed to assist in the film unit being firmly united after processing. Such a hydrophilic polymer layer prevents, after the formation of a diffusion transfer color image is substantially complete, further transfer of the colored component into the image receiving layer to thereby help prevent image changes.

In some cases, it is advantageous that the processing compositions also contain light absorbing substances such as $TiO_2$, carbon black, pH indicators, or desensitizers as described in U.S. Pat. No. 3,579,333, in order to prevent a silver halide(s) from being fogged by an external light. In addition, the processing compositions can also contain development inhibitors such as benzotriazole. The aforesaid processing compositions can be used by encasing the same in a rupturable container as described in U.S. Pat. Nos. 2,543,181, 2,643,886, 2,653,732, 2,723,051, 3,056,491, 3,056,492 and 3,152,515, etc.

According to the method of this invention, detection sensitivity of trace components is high and excellent results of precise accuracy and reproducibility are obtained.

The markers used in the method of this invention do not involve the hazards of radiation as does radioimmunoassay since the markers, i.e., fogging agents, are not radioactive; measurement and inspection can easily be performed by a person not necessarily qualified to deal with radioactives and, in addition, storage of the markers for a long period of time due to the excellent stability thereof is possible. Further, densitometers as are conventionally used in the photographic arts can be used as measurement equipment so that measurement can be made simply and at low cost.

In the following examples, all percents are by weight, and reactions were performed at ambient temperature under atmospheric pressure, unless otherwise indicated.

EXAMPLE 1

In 10 ml. of a 6 M urea-0.05 M tris-hydroxymethylaminomethanehydrochloric acid buffer solution of pH 8.0, 2 mg. of bovine serum albumin (manufactured by Sigma Chemicals Co., Ltd.) was dissolved (A solution).

A fogging agent (5 mg.) having formula I:

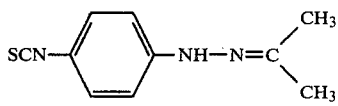

was dissolved in 10 ml. of dimethyl formamide (B-solution).

While stirring the B-solution under ice cooling, the A-solution was added thereto, followed by reacting for 30 secs. at 4° C. and for further 1 hr. at room temperature. Immediately after completion of the reaction, the labelled albumin formed was separated using a Sephadex G-10 column which had been previously substituted with 0.2 M ammonia water sufficiently. The thus separated labelled albumin was then purified using an ion exchange resin (diethylaminoethyl cellulose; weakly basic) to obtain albumin labelled with the fogging agent, of high purity.

In order to prepare a calibration curve, unlabelled albumin was dissolved in a buffer solution having the same composition as above to obtain standard solutions containing unlabelled albumin in amounts of zero, 5, 10, 20, 40, 80, 160 and 320 $\mu U/ml$, respectively. Each of the standard solutions was then taken in a small test tube in an amount of 100 $\mu l$ and a 0.1 M boric acid buffer solution (0.5 ml.) of pH 8.6 was added thereto. Into each of the respective test tubes, 100 $\mu l$ of the labelled albumin solution (100 $\mu g/ml$) was charged, respectively, and 100 $\mu l$ of a diluted buffer solution of rabbit antiserum of bovine serum albumin (manufactured by Dynabot Radioisotope Co., Ltd., Tokyo) was further added thereto. After thoroughly stirring the mixture, the system was allowed to stand for 16 hrs. at 4° C. The resulting reaction liquid was subjected to B/F separation using Sephadex G-75 which had been brought into equilibrium using 0.1 M boric acid. Thus, the labelled albumin fraction unbound to the antibody was collected.

Each of the thus obtained fractions (10 $\mu l$) was dropwise added onto a 5 mm$\phi$ area of a photographic film comprising a support (PET) having coated thereon an unexposed emulsion (AgBrCl; Br content 80 mol%, average grain size 0.6 $\mu ml$; binder, gelatin:PVA=50:50, thickness 4$\mu$, Ag amount coated 5 g/m², Ag/binder=about 1:2 by weight). After allowing the system to stand for 5 mins., the system was then developed with a Developer having the composition below, at 20 C. for 5 mins.

| Composition of Developer: | |
| --- | --- |
| Metol | 0.31 g. |
| Sodium hydrogen sulfite | 39.6 g. |
| Hydroquinone | 6.0 g. |
| Sodium carbonate (monohydrate) | 21.9 g. |
| Potassium bromide | 0.86 g. |
| Citric acid | 0.68 g. |
| Potassium metabisulfite | 1.50 g. |
| Water to make 1 liter. | |

Following the development, fixing, washing and drying were carried out in succession in a conventional manner. The black density of the fogged area of the photographic film thus processed was measured in a conventional fashion using a densitometer manufactured by Fuji Photo Film Co., Ltd. The results obtained are shown in Table I.

TABLE I

| Concentration of Albumin Standard Solution ($\mu v/ml$) | Black Density |
| --- | --- |
| 0 | 0.15 |
| 5 | 0.30 |
| 10 | 0.61 |
| 20 | 0.95 |
| 40 | 1.32 |
| 80 | 1.68 |
| 160 | 2.01 |
| 320 | 2.40 |

Based on the data obtained above, a calibration curve for use in quantitative analysis of an unknown amount of albumin was obtained and is shown in the FIGURE.

With respect to a solution containing an unknown amount of albumin, the same procedures as above were repeated. From the thus obtained black density data, a concentration of albumin was read using the calibration curve shown in the FIGURE.

While the emulsion (layer) having a specific composition was used in this example, the kind of binder, thickness of an emulsion layer Ag amount coated, etc., can be varied depending upon necessity; these are well known to one skilled in the art and it is not deemed to require further explanation. However, in general, the amount of silver coated ranges from about 1 to 30 g./m² and a thickness of an emulsion layer from about 1 to about 40 microns.

The kind and thickness of a support can also be easily chosen by one skilled in the art; but, in general, PET, TAC, paper, etc., are typically used and the thickness ranges from about 50 to about 300 microns.

Hereafter, unless otherwise indicated, the same procedures, compositions, and reaction conditions as described above were used in the following examples.

EXAMPLE 2

100 mg. of insulin was dissolved in 10 ml. of a 0.01 M tris hydrochloric acid buffer solution. To the resulting solution, 100 mg. of a fogging agent of formula(II):

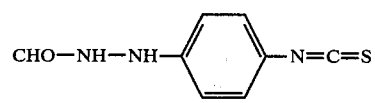

was added. The mixture was reacted as follows to mark the insulin: the reaction mixture was subjected to gel filtration, i.e., desalted with Sephadex G-25 which had been completely substituted with a 1 M aqueous acetic acid solution, to obtain an insulin fraction marked with the fogging agent. The thus obtained insulin fraction was further purified with DEAE cellulose.

The thus purified marked insulin was taken in a fixed amount and added to a solution containing an unknown concentration of insulin. After mixing and allowing the system to reach equilibrium (allowing the system to stand for 16 to 24 hrs. at 4° C.), 100 $\mu l$ of anti-guinea pig gamma-G-sheep diluted serum (second antibody, manufactured by Dynabot Radioisotope Co., Ltd.). The mixture was shaken to mix and incubated for 16 hrs. at 4° C. After completion of the incubation, the reaction mixture was subjected to B/F separation by means of centrifugation at 3,600 rpm for 30 minutes.

To an area of 5 mm$\phi$ on a photographic film comprising a support (PET or TAC) having coated thereon an unexposed AgBrI emulsion (I=5 mol%, average grain size, 0.7$\mu$), 10 ml. of the supernatant remaining after removing the precipitate resulting from centrifugation was dropwise added. After allowing the system to stand for 10 mins., the system was developed at 20° C. for 5 mins. using Developer A having the composition given below, followed by fixing, rinsing with water and drying in a conventional manner. The black density of the thus obtained photographic film was then determined in a conventional fashion with a densitometer manufactured by Fuji Photo Film Co., Ltd.

Separately, a solution containing a known concentration of insulin was prepared. The procedure described as in Example 1 was conducted to obtain a calibration curve.

Using the calibration curve, the amount of insulin contained in the solution at unknown concentration was determined.

The binder composition used in the emulsion above was gelatin:agar=50:50 and the Ag amount coated was 4 g/m$^2$.

| Developer A | |
|---|---|
| Metol | 3.1 g. |
| Sodium sulfite | 45 g. |
| Hydroquinone | 12 g. |
| Sodium carbonate (anhydrous) | 67.5 g. |
| KBr | 1.9 g. |
| Water to make 1 liter. | |

EXAMPLE 3

Antiinsulin was marked as in Example 1 except that the following compound (III):

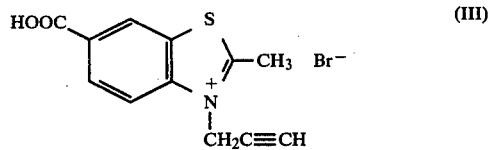

was used in place of fogging agent (I).

By the same procedure as in Example 1, the concentration of antiinsulin of an unknown amount was determined.

EXAMPLE 4

Albumin was marked with a carbocyanin compound having the following structure:

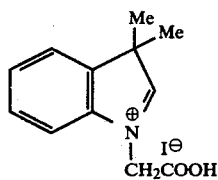

After separating and purifying the marked albumin, 100 mg of the marked albumin was dissolved in 1 l. of deionized water (Sample a).

Separately, 80 mg of antialbumin was dissolved in 1 l. of deionized water (Sample b).

1 ml was taken from each of the Samples a and b with a pipet and put in a test tube. Samples a and b were then reacted therein.

The resulting mixture was separated by gel filtration to obtain the unreacted marked albumin (Sample c). Separately, various solutions having different known concentrations of albumin were prepared. These solutions were reacted with the marked albumin as above, whereafter unreacted marked albumin having various concentrations was separated (Sample d).

Next, 500 $\mu$l of each of Samples b, c and d was dropwise added to an area of 5 mm$\phi$ of photographic films having coated thereon an unexposed emulsion. After standing for 10 mins., the systems were developed with Developer B having the composition given below at 20° C. for 10 mins., followed by fixing, rinsing and drying in a conventional manner. The binder composition in the emulsion was (gelatin:acrylamide=50:50) and Ag was coated in an amount of 3.5 g/m$^2$.

| Developer B | |
|---|---|
| Metol | 4.8 g. |
| Sodium sulfite | 48 g. |
| Hydroquinone | 10 g. |
| Borax pentahydrate | 10 g. |
| Sodium hydroxide | 9 g. |
| Sodium bisulfite | 3.5 g. |
| Potassium bromide | 4.5 g. |
| Water to make 1 liter. | |

The degree of blackening of the thus obtained photographic films was determined in a conventional manner using a densitometer manufactured by Fuji Photo Film Co., Ltd.

In addition, 1.0 ml of an antialbumin solution having an unknown concentration was mixed and reacted with Sample a. The formed reaction mixture was separated as above and the obtained unreacted marked albumin solution was dropwise added in an amount of 10 $\mu$l to an area of 5 mm$\phi$ to photographic films having coated thereon an unexposed emulsion as described above. After standing for 10 mins., developing, fixing, rinsing and drying were conducted as above, whereafter the degree of blackening of each of the thus obtained photographic films was measured as above. From the thus determined density values and the calibration curve obtained as earlier described, the unknown concentration of albumin was determined. The results were in agreement with the calculated amount. It was thus confirmed that the method of this invention was highly accurate and highly sensitive.

EXAMPLE 5

Quantitative analysis of antialbumin was performed in a manner similar to Example 1 except that the albumin was marked with compound (IV) as in Example 4. Good results were similarly obtained.

While the invention has been described in detail and with reference to specific embodiments thereof, it will be apparent from one skilled in the art that various changes and modifications can be made therein without departing from the spirit and scope thereof.

What is claimed is:

1. A method for performing a competitive immunoassay for a trace component in a sample comprising:
   (1) adding a labeled antigen or labeled antibody to said sample in a competitive immunoassay protocol, said label being a silver halide fogging agent,
   (2) permitting the immune reactions to take place,
   (3) separating the free labeled antigen or free labeled antibody from the resulting bound labeled antigen or bound labeled antibody,
   (4) developing silver halide in the presence of either free or bound labeled antigen or free or bound labeled antibody, and
   (5) measuring the optical density resulting from step (4).

2. The competitive immunoassay of claim 1 wherein said silver halide fogging agent is a chemical sensitizer for photography.

3. The competition immunoassay of claim 2 wherein said chemical sensitizer is capable of fogging silver halide and is selected from the group consisting of a sulfur-containing compound, a reducible compound and a metal complex.

4. The competitive immunoassay of claim 3 wherein said sulfur-containing compound is selected from the group consisting of a compound having a thiocarbonyl group(A), a compound having a thioether group(B), a thiosulfuric acid, a thiophosphoric acid and derivatives thereof.

5. The competition immunoassay of claim 4 wherein said compound(A) is selected from the group consisting of thiourea, a dithiocarbamate, a trithiocarbonate, a dithio ester, a thioamide, a rhodanine, a thiohydantoin, a thiosemicarbazide and derivatives thereof.

6. The competitive immunoassay of claim 4 wherein said compound (B) is selected from the group consisting of a sulfide, a disulfide and a polysulfide.

7. The competitive immunoassay of claim 3 wherein said reducible compound is selected from the group consisting of a hydrazine, a hydrazone, an amine, a polyamine, a cyclic amine, a hydroxylamine, a quaternary amine salt and derivatives thereof.

8. The competitive immunoassay of claim 7 wherein said hydrazine is 4-(2-formylhydrazino)phenylisothiocyanate.

9. The competitive immunoassay of claim 7 wherein said hydrazone is 2-(2-isopropylidenehydrazino)phenyl isothiocyanate.

* * * * *